United States Patent
Saika et al.

(10) Patent No.: US 6,203,900 B1
(45) Date of Patent: Mar. 20, 2001

(54) PRESSURE SENSITIVE ADHESIVE SHEET FOR DETECTION OF MICROORGANISM AND METHOD FOR DETECTION OF MICROORGANISM

(75) Inventors: Takeshi Saika; Shuji Senda; Yoshitaka Kazuse; Akio Iwama; Tetsuji Sugii, all of Ibaraki; Masao Nasu, Osaka; Katsuji Tani, Takatsuki; Nobuyasu Yamaguchi, Ibaraki, all of (JP)

(73) Assignee: Nitto Denko Corporation, Osaka (JP)

( * ) Notice: Subject to any disclaimer, the term of this patent is extended or adjusted under 35 U.S.C. 154(b) by 0 days.

(21) Appl. No.: 08/885,848

(22) Filed: Jun. 30, 1997

(30) Foreign Application Priority Data

| Jun. 28, 1996 | (JP) | 8-169279 |
| Jun. 28, 1996 | (JP) | 8-169281 |
| May 20, 1997 | (JP) | 9-129580 |
| May 20, 1997 | (JP) | 9-129586 |

(51) Int. Cl.[7] ............................................. B32B 15/04
(52) U.S. Cl. ................ 428/343; 428/350; 428/355 AC; 435/30
(58) Field of Search ................... 428/343, 350, 428/355 AC; 435/30

(56) References Cited

U.S. PATENT DOCUMENTS

| 3,660,147 | * 5/1972 | Van Hoot et al. | 428/355 AC |
| 5,232,838 | 8/1993 | Nelson et al. | 435/30 |
| 5,700,769 | * 12/1997 | Schneider et al. | 510/305 |
| 5,707,950 | * 1/1998 | Kasturi et al. | 510/320 |

FOREIGN PATENT DOCUMENTS 2019434  10/1979 (GB).

* cited by examiner

Primary Examiner—Blaine Copenheaver
Assistant Examiner—John J. Guarriello
(74) Attorney, Agent, or Firm—Sughrue, Mion, Zinn, Macpeak & Seas, PLLC

(57) ABSTRACT

A pressure sensitive adhesive sheet for the detection of microorganisms, which comprises a laminate of an adhesive layer mainly composed of a water-soluble polymer and a water-permeable membrane which does not allow passage of the microorganisms; a pressure sensitive adhesive sheet for the detection of microorganisms, wherein the surface of the adhesive layer has a contact angle with water of not more than 90°; and a method for detecting a microorganism, which comprises bringing the surface of an adhesive layer of a pressure sensitive adhesive sheet into contact with the surface of a test object, and then bringing the surface of the adhesive layer into contact with water, said adhesive layer or water containing a chromogenic reagent. The use of the laminate makes it possible to leave only stained microorganisms on the water-permeable membrane and to precisely observe the color developed by the microorganisms. The method of the present invention enables real-time monitoring without culture of microorganisms, and is not limited to the detection of viable cells alone. Inasmuch as a contact of the pressure sensitive adhesive sheet with a test face results in accumulation of microorganisms, the manipulation is simple. In addition, by properly determining a chromogenic reagent, a specific microorganism alone can be detected and counted, so that it can be applied to environmental investigation in the medical field, food industry field and the like.

27 Claims, 1 Drawing Sheet

PRESSURE SENSITIVE ADHESIVE SHEET FOR DETECTION OF MICROORGANISM AND METHOD FOR DETECTION OF MICROORGANISM

TECHNICAL FIELD OF THE INVENTION

The present invention relates to a pressure sensitive adhesive sheet for the detection of microorganisms on the surface of a test object (hereinafter said surface is also referred to as a test surface) or counting said microorganisms, and to a method for the detection of microorganisms using the pressure sensitive adhesive sheet.

BACKGROUND OF THE INVENTION

For observation of microorganisms such as bacteria which are present on a test surface but cannot be visually observed, there has heretofore been applied a culture method wherein a microorganism is allowed to form a colony. According to this method, a solid plate medium using an agar and the like is pressed against the test surface to transfer the microorganisms on the test surface to the agar plate medium; microorganisms are cultured as they are under the optimal environment; and the colonies formed on the agar plate medium are counted visually. Examples of this method include a food stamp method using an agar stamp commercially available from Nissui Pharmaceutical Co., Ltd. and membrane filter method.

According to the membrane filter method which uses a commercially available membrane filter capable of trapping microorganisms, the microorganisms are collected by thoroughly wiping a test surface with saline, phosphate buffer and the like and filtering the pooled aqueous solution through a membrane filter and the like to trap the microorganisms on the membrane filter. The obtained microorganisms are sufficiently brought into contact with a liquid medium to allow formation of colonies on the filter, and the colonies are counted.

In addition, Igaku Kensa (Medical Test), vol. 41, No. 3, p. 352 (1992) discloses, as an example of culture method, a film coat method including preparation of a film coated with a medium, bringing same into contact with a test surface and culturing same to harvest the detection target microorganism.

A method such as food stamp method, nevertheless, is often associated with insufficient collection efficiency of microorganisms, since it has weak adhesive strength available for transferring microorganisms by pressing a medium against a test surface, and is poor in reproducibility because of variable water contents of the agar medium. Being commonly problematic in various culture methods, contamination among microorganisms is inevitable, which in turn results in interaction among microorganisms on the medium and precludes pure culture, whereby ultimate identification analysis cannot be performed. What is more, not every microorganism is capable of culture to form colonies on a medium and the culture method is limited to the detection of viable cells alone, exclusive of microorganisms that cannot grow in an ordinary medium; thus the method is associated with possible omission of detection. A material limitation on the culture method is that culture time of 1–2 days or longer is needed, so that a real-time monitoring of microorganism detection is not possible.

In the membrane filter method, moreover, a liquid test object such as an aqueous solution can pass through a filter as it is, but other non-liquid test objects require accumulation of microorganisms by time-consuming cumbersome steps of sampling with a cotton swab, preparation of solutions for washing, and the like. In addition, this method does not elude the above-mentioned defects of the culture method, since the determination of microorganisms is based on the culture and the number of colonies formed on a filter by culture. The film coat method also suffer from various defects of the culture method.

The technique recently developed to detect ATP (adenosine triphosphate) in the cells of microorganisms is only applicable to the microorganisms dispersed in water, so that the method for collecting the microorganisms has been the difficult part. As such, there has not been available an easy and simple method for detection of microorganisms in the prior art techniques.

SUMMARY OF THE INVENTION

It is therefore an object of the present invention to solve the above-mentioned defects of the conventional methods and enable real-time monitoring of the detection and determination of microorganisms such as bacteria.

That is, the present invention provides the following.

1) A pressure sensitive adhesive sheet for the detection of microorganisms, which comprises a laminate of an adhesive layer mainly composed of a water-soluble polymer and a water-permeable membrane which does not allow passage of the microorganisms.
2) The sheet of 1) above, wherein the water-permeable membrane is supported by a water-permeable support.
3) The sheet of 1) above, wherein the water-soluble polymer is easily dissolved in water and passes through the water-permeable membrane when dissolved in water.
4) The sheet of 1) above, wherein the surface of the water-permeable membrane on the adhesive layer side has a smoothness of not more than 20 $\mu$m.
5) The sheet of 1) or 2) above, wherein the surface of the adhesive layer has a contact angle with water of not more than 90°.
6) A pressure sensitive adhesive sheet for the detection of microorganisms, which comprises an adhesive layer having a contact angle with water of not more than 90° and a support, the adhesive layer being formed on the support.
7) The sheet of 1) or 6) above, which has a thickness of 10–100 $\mu$m and an adhesive strength to a Bakelite board of 30 g/12 mm width to 600 g/12 mm width.
8) The sheet of 1) or 6) above, wherein the adhesive layer comprises a chromogenic substrate.
9) The sheet of 8) above, wherein the chromogenic substrate is one member selected from 3-(3,4-dihydroxyphenyl) alanine, 3,3',5,5-tetramethylbenzidine and nitro blue tetrazolium.
10) The sheet of 1) or 6) above, wherein the adhesive layer comprises an enzyme.
11) The sheet of 10) above, wherein the enzyme is a phenoloxidase.
12) The sheet of 1) or 6) above, wherein the adhesive layer comprises a chromogenic substrate and an enzyme.
13) The sheet of 1) or 6) above, wherein the adhesive layer comprises an enzyme-labeled antibody.
14) The sheet of 13) above, wherein the enzyme-labeled antibody is against microorganism surface antigen and labeled with a peroxidase or alkaline phosphatase.
15) The sheet of 1) or 6) above, wherein the adhesive layer comprises an enzyme-labeled antibody and a chromogenic substrate.
16) The sheet of 1) or 6) above, wherein the adhesive layer comprises a chromogenic substance.
17) The sheet of 16) above, wherein the chromogenic substance is a fluorescent dye.

18) A method for detecting a microorganism, which comprises bringing the surface of an adhesive layer of a pressure sensitive adhesive sheet into contact with the surface of a test object, and then bringing the surface of the adhesive layer into contact with water, said adhesive layer or water containing a chromogenic reagent.

19) The method of 18) above, wherein the surface of the adhesive layer of the pressure sensitive adhesive sheet of 1) or 6) above is brought into contact with the surface of a test object, and then the surface of the adhesive layer is brought into contact with an aqueous solution containing an enzyme and a chromogenic substrate.

20) The method of 18) above, wherein the sheet is that of 1) or 6) above, the adhesive layer thereof comprising a chromogenic substrate, and the surface of the adhesive layer is brought into contact with an aqueous solution containing an enzyme, after contact of the surface of said adhesive layer with the surface of the test object.

21) The method of 18) above, wherein the sheet is that of 1) or 6) above, the adhesive layer thereof comprising an enzyme, and the surface of the adhesive layer is brought into contact with an aqueous solution containing a chromogenic substrate, after contact of the surface of said adhesive layer with the surface of the test object.

22) The method of 18) above, wherein the sheet is that of 1) or 6) above, the adhesive layer thereof comprising a chromogenic substrate and an enzyme, and the surface of the adhesive layer is brought into contact with water, after contact of the surface of said adhesive layer with the surface of the test object.

23) The method of 18) above, wherein the sheet is that of 1) or 6) above, and the surface of the adhesive layer is brought into contact with an aqueous solution containing an enzyme-labeled antibody against the microorganism to be detected and a chromogenic substrate, after contact of the surface of said adhesive layer with the surface of the test object.

24) The method of 18) above, wherein the sheet is that of 1) or 6) above, the adhesive layer thereof comprising an enzyme-labeled antibody against the microorganism to be detected, and the surface of the adhesive layer is brought into contact with an aqueous solution containing a chromogenic substrate, after contact of the surface of said adhesive layer with the surface of the test object.

25) The method of 18) above, wherein the sheet is that of 1) or 6) above, the adhesive layer thereof comprising an enzyme-labeled antibody against the microorganism to be detected and a chromogenic substrate, and the surface of the adhesive layer is brought into contact with water, after contact of the surface of said adhesive layer with the surface of the test object.

26) The method of 18) above, wherein the sheet is that of 1) or 6) above, and the surface of the adhesive layer is brought into contact with an aqueous solution containing a chromogenic substance, after contact of the surface of said adhesive layer with the surface of the test object.

27) The method of 18) above, wherein the sheet is that of 1) or 6) above, the adhesive layer thereof comprising a chromogenic substance, and the surface of the adhesive layer is brought into contact with water, after contact of the surface of said adhesive layer with the surface of the test object.

BRIEF DESCRIPTION OF THE DRAWINGS

FIG. 2 is a cross section of one embodiment of the pressure sensitive adhesive sheet 1a of the present invention, which comprises a water-permeable membrane 4, an adhesive layer 2a mainly composed of a water-soluble polymer and a support 3a.

DETAILED DESCRIPTION OF THE INVENTION

Figure 1:
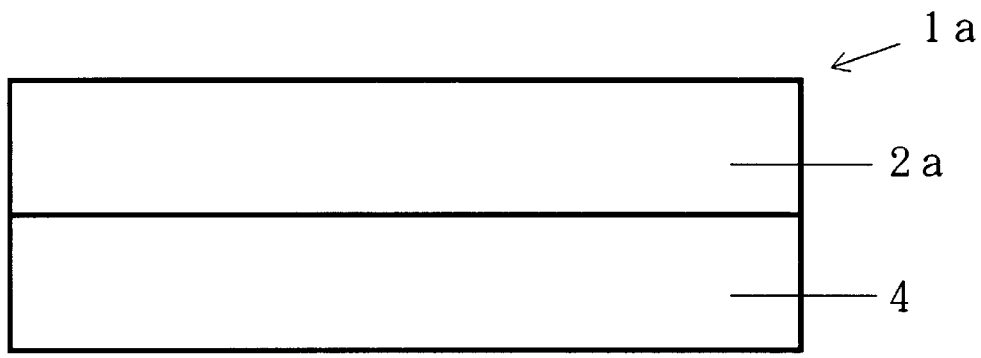
FIG. 1 is a cross section of one embodiment of the pressure sensitive adhesive sheet 1a of the present invention, which comprises a water-permeable membrane 4 and an adhesive layer 2a mainly composed of a water-soluble polymer.

The pressure sensitive adhesive sheet of the present invention is exemplified by the embodiment of 1) above which is shown in FIG. 1. In FIG. 1, (1a) is a pressure sensitive adhesive sheet for detecting microorganisms, wherein an adhesive layer (2a) mainly composed of a water-soluble polymer is laminated on a water-permeable membrane (4). In this embodiment, the adhesive layer of the pressure sensitive adhesive sheet of the present invention has a tackiness, as well as a smooth surface structure and a suitable amount of water where necessary. The adhesive in said adhesive layer should collect microorganisms on the test surface, and be free of visible remainder thereof on said test surface after release of the sheet. In other words, the adhesive layer (2a) in this embodiment is mainly composed of a water-soluble polymer, is water soluble as a whole, preferably completely soluble in water, and comprises only components that quickly pass through holes of the water-permeable membrane.

By water soluble as a whole is meant that 0.5 g of an adhesive completely dissolves in 30 ml of distilled water in 25 minutes at room temperature.

A sufficient contact between the adhesive surface and the aqueous solution containing a chromogenic reagent can be facilitated by setting the contact angle of the adhesive layer (2a) with water to not more than 90°, as mentioned later, and sufficient recovery ratio of microorganisms can be achieved by pressing the adhesive surface against the test surface for transfer and collection of microorganisms when the adhesive layer (2a) is designed to have a peel adhesion of not less than 30 g/12 mm, preferably not less than 80 g/12 mm width, and not more than 600 g/12 mm width, preferably not more than 400 g/12 mm width, relative to a Bakelite board. A thickness of the adhesive layer (2a) of 10–100 $\mu$m, preferably 20–80 $\mu$m, and more preferably 30–60 $\mu$m, provides a desired peel adhesion without cohesion failure of adhesive layer upon release.

Examples of the water-soluble polymer which is the main component of adhesive layer (2a) in the instant embodiment include agar, carrageenin, gum arabic, gelatin, water-soluble natural polymer such as carboxymethyl cellulose, polymer obtained by polymerization of water-soluble monomers such as vinylpyrrolidone, vinyl alcohol, 2-hydroxyethyl acrylate, 2-methoxyethyl acrylate, vinyl ether and acrylic acid, and copolymer of two or more of these water-soluble monomers.

Preferred water-soluble polymer includes, for example, acrylic copolymer of alkoxyalkyl acrylate and N-vinyl lactam.

The alkoxyalkyl acrylate which is a monomer component of acrylic copolymer is preferably an acrylate having a $C_1$–$C_4$ alkoxy group and a $C_2$–$C_4$ alkylene or alkylene glycol group. Specific examples include alkoxyalkyl acrylates and alkoxyalkylene glycol acrylates such as 2-methoxyethyl acrylate, 2-ethoxyethyl acrylate, 2-butoxyethyl acrylate, 3-methoxypropyl acrylate, 3-methoxybutyl acrylate, 3-ethoxypropyl acrylate, 3-ethoxybutyl acrylate, butoxytriethylene glycol acrylate, 2-(2-ethoxyethyl)ethyl acrylate, methoxytriethyleneacrylate, methoxydipropylene glycol acrylate and the like. Preferred are 2-methoxyethyl acrylate and 2-ethoxyethyl acrylate having high hydrophilicity.

Examples of N-vinyl lactam which is the other monomer component include 5 to 7-membered ring, N-vinyl lactam. For example, N-vinyl-2-pyrrolidone, N-vinyl-2-piperidone, N-vinyl-2-caprolactam and the like can be used, with preference given to N-vinyl-2-pyrrolidone in terms of safety and wide applicability.

The alkoxyalkyl acrylate content is preferably 60–80 wt %, and more preferably 65–75 wt %, of the entire acrylic copolymer. When the alkoxyalkyl acrylate content is less than 60 wt %, the obtained adhesive layer sometimes shows lower flexibility. On the other hand, when it exceeds 80 wt %, the adhesive layer tends to have greater tackiness and smaller strength.

The N-vinyl lactam is contained in a proportion of 20–40 wt %, and more preferably 25–35 wt %, of the entire acrylic copolymer. When the N-vinyl lactam content is less than 20 wt % of the acrylic copolymer, the obtained adhesive layer sometimes shows lower strength and poor water absorption. On the other hand, when it exceeds 40 wt %, the obtained adhesive layer sometimes has lower flexibility, and acrylic copolymer may dissolve in water and liquidized.

The above-mentioned water-soluble polymer may be copolymerized with alkyl acrylate having a $C_1$–$C_8$ alkyl group, such as ethyl acrylate and butyl acrylate, as long as water solubility is not impaired.

The water-soluble polymer can be prepared by a method known per se. For example, acrylic copolymer can be produced by any polymerization method such as solution polymerization, emulsion polymerization, suspension polymerization, bulk polymerization, photopolymerization and the like.

The above-mentioned composition may contain a hydrophilic or water-soluble low molecular substance to impart suitable tackiness. Examples of hydrophilic or water-soluble low molecular substance include liquid compounds having a high boiling point and deliquescent inorganic salts. The liquid compound having a high boiling point preferably has a boiling point of 100–400° C., preferably 200–350° C. Specific examples thereof include polyhydric alcohol and sugar alcohol. Polyhydric alcohol includes, for example, ethylene glycol, diethylene glycol, triethylene glycol, liquid poly(ethylene glycol), propylene glycol, dipropylene glycol, 1,1,1-trihydroxypropane, glycerin and the like, and sugar alcohol includes, for example, sorbitol and sorbitan. Polyoxyethylene glyceryl ether and polyoxypropylene glyceryl ether which are ether adducts of glycerin with ethylene glycol or propylene glycol can be also used. Also, it may be polyoxypropylene sorbitol ether and polyoxyethylene sorbitan ether which are ether adducts of sorbitol or sorbitan with ethylene glycol or propylene glycol.

The deliquescent inorganic salts include, for example, lithium nitrate, lithium chloride and the like.

These hydrophilic and water-soluble low molecular substances are added in a proportion of 5–90 wt % of the adhesive forming the adhesive layer.

The adhesive layer (2a) may contain a chromogenic reagent to be mentioned later, whereby preparation of a solution containing the chromogenic reagent and contact thereof with an adhesive surface can be obviated during detection of microorganisms.

The water-permeable membrane (4) allows permeation of dissolved water-soluble polymer upon color production, but does not allow permeation of the microorganisms attached to the surface of the adhesive layer. Such water-permeable membrane is exemplified by pulp filter paper, cellulose acetate membrane, nylon membrane, polycarbonate membrane, polytetrafluoroethylene membrane, glass filter, nitrocellulose membrane, polyvinylidene fluoride membrane, silver filter, cellulose acetate/nitrocellulose blend membrane, ethylene vinylacetate copolymer membrane, membrane composed of hydrolysate of ethylene vinylacetate copolymer, polyether sulfone membrane, polyvinyl acetal membrane, polysulfone membrane, regenerated cellulose membrane, polyacrylonitrile membrane, polyethylene filter, polypropylene filter and the like.

The pore size of water-permeable membrane (4) is required to be smaller than that of microorganisms, so that the microorganisms can be captured on the surface of the membrane. Typical microorganisms include, for example, eumycetes (e.g., mold), bacteria and virus. The pore size of the water-permeable membrane (4) is not more than 10 $\mu$m, preferably not more than 4 $\mu$m, more preferably not more than 2 $\mu$m, though it may vary depending on the target microorganisms. For sufficient water permeability to be imparted and water-soluble polymer after dissolution to be passed, the pore size of the water-permeable membrane (4) is not less than 0.01 $\mu$m, preferably not less than 0.05 $\mu$m, and more preferably not less than 0.1 $\mu$m.

For easy counting of the collected microorganisms with a microscope, the face of the water-permeable membrane (4) to be laminated with the adhesive layer preferably has a smoothness (difference between concave and convex surfaces) of not more than 20 $\mu$m. The smoothness can be determined by observation of the cross section of water-permeable membrane (4) with an electron microscope and obtaining the difference between the top of a convex surface and the bottom of a concave surface of the membrane. When the smoothness is not more than 20 $\mu$m, the microscope can be focused on the microorganisms, thus facilitating counting.

Figure 2:
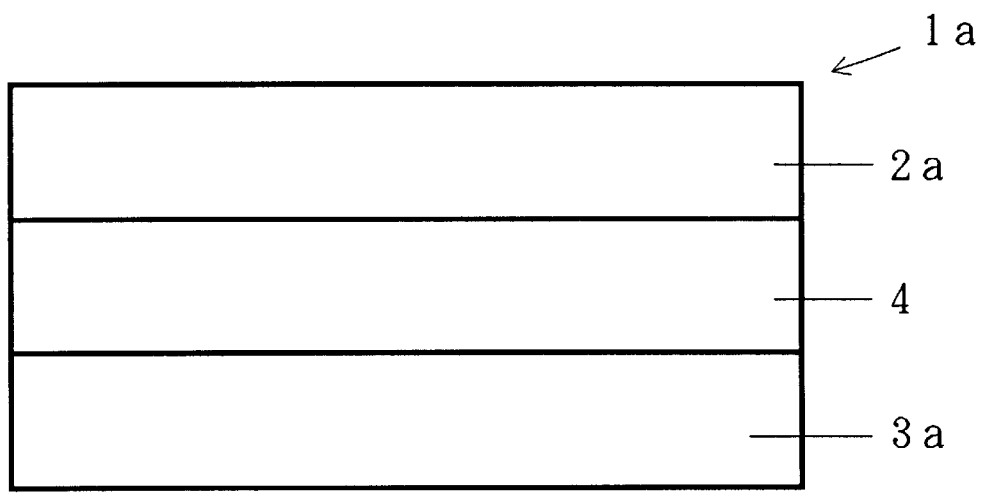

The pressure sensitive adhesive sheet of the present invention consisting of adhesive layer (2a) mainly composed of a water-soluble polymer and water-permeable membrane (4) may be laminated on a support (3a) to support the water-permeable membrane (4), as shown in FIG. 2. The support (3a) is subject to no particular limitation as long as it has a sufficient strength to endure bending and flexibility to allow free application of pressure sensitive adhesive sheet (1a) by pressing same against curved surfaces and narrow surfaces. When the pressure sensitive adhesive sheet after detection of microorganisms is disposed in a funnel of a filtration filter and subjected to filtration under reduced pressure, a water-permeable support is preferably used for easy suction. Examples of the water-permeable support include paper, woven fabric, nonwoven fabric and porous film, which are water-permeable themselves, and water-impermeable paper, woven fabric, nonwoven fabric and porous film which can be made water-permeable by forming through-holes. For example, polyethylene laminated paper; nonwoven fabric, such as rayon, polyester and cotton, which is laminated on polypropylene; paper subjected to sizing treatment; and hydrophilic-treated film, which are made water-permeable by forming holes from the support side with a perforating roller after forming an adhesive layer, can be used.

The pressure sensitive adhesive sheet (1a) of the present invention in this embodiment can be produced by a method known Per se. For example, an aqueous solution containing a water-soluble polymer and a hydrophilic low molecular substance is applied to a water-permeable membrane and dried at 10° C.–200° C. Alternatively, an adhesive layer containing a water-soluble polymer and a hydrophilic low molecular substance is laminated on a water-permeable membrane. Further, the pressure sensitive adhesive sheet can be laminated on a support.

Particularly when the water-soluble polymer is an acrylic copolymer, superior thermoplasticity of the acrylic copolymer affords superior processability when forming same into a film or sheet by extrusion molding. The extrusion molding can be an inflation molding, T die molding, lamination molding or other generally known molding method. The extruder may be a single screw extruder or double screw extruder. By appropriately adjusting molding conditions such as molding temperature, die lip width, extrusion rate and take-up rate, the thickness of film and sheet can be controlled. In this case, molding temperature is preferably not less than 140° C. and not more than 180° C., more preferably not less than 150° C. and not more than 170° C.

The film and sheet can be formed by calender method, casting method and the like. The sheet thus obtained can be cut into an optional shape and used as a pressure sensitive adhesive sheet (1a).

Figure 3:
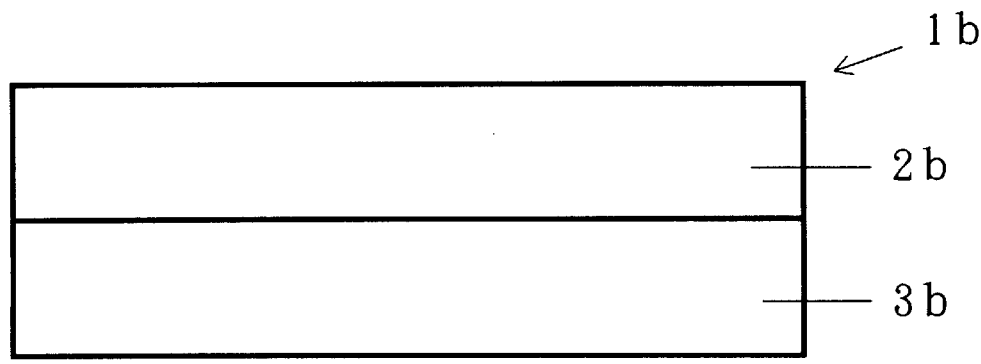
FIG. 3 is a cross section of one embodiment of the pressure sensitive adhesive sheet 1b of the present invention, which comprises an adhesive layer 2b having a contact angle with water of not more than 90° and a support 3b.

Another embodiment of the pressure sensitive adhesive sheet of the present invention is described in the above 5) and shown in FIG. 3. In FIG. 3, (1b) is a pressure sensitive adhesive sheet for detection of microorganisms, wherein an adhesive layer (2b) having a contact angle with water of not more than 90° is laminated on a support (3b).

In this embodiment, the adhesive layer (2b) of the pressure sensitive adhesive sheet of the present invention has tackiness and sufficient wettability by an aqueous solution, and is formed, for example, on a flexible support (3b) having a sufficient strength to endure bending.

In the present invention, the contact angle with water means an angle which is formed by a tangent from a water drop and the adhesive face of said adhesive layer, and which is the angle on the same side with the water drop. In this embodiment, the pressure sensitive adhesive sheet of the present invention has a contact angle with water which is in the range of from negligibly exceeding 0° to not more than 90°, with preference given to an angle of not more than 30°, more preferably not more than 10°. When the contact angle is greater than 90°, the adhesive face on which microorganisms such as bacteria have been attached or collected cannot be brought into sufficient contact with an aqueous solution containing a chromogenic reagent to be mentioned later, and a specific biochemical response cannot be induced in a highly sensitive manner in the entirety of the adhesive face, when the amount of the microorganisms is small. When the contact angle with water is substantially 0°, the wettability of the adhesive face by water is perfect and the adhesive face on which microorganisms such as bacteria have been attached or collected can be brought into sufficient contact with an aqueous solution containing a chromogenic reagent, whereby a specific biochemical response can be induced in a highly sensitive manner in the entirety of the adhesive face, with a trace amount of the microorganisms.

In the present invention, the contact angle with water can be determined using a FACE automatic contact angle meter CA-X type (manufactured by KYOWA INTERFACE SCIENCE CO., LTD.) under the following conditions.
(1) droplet: adjusted to about 0.9 µl by sessile drop method
(2) temperature: 25° C.
(3) determination: after 30 sec from dropping of liquid Said adhesive layer (2b) is preferably a water-soluble polymer or a crosslinked product thereof. As the water-soluble polymer, those mentioned above can be used in the same manner.

In this embodiment, the water-soluble polymer may be an adhesive polymer wherein hydrophobic monomer, such as butyl acrylate and 2-ethylhexyl acrylate, has been copolymerized, or may be a polysaccharide polymer, such as hydrophilic polyether urethane polymer, stilbazolium polyvinyl alcohol, xanthane gum and the like, as long as it satisfies the requirements of adhesive layer (2b), namely, as long as the contact angle with water does not deviate from the range of not greater than 90°.

It is also preferable to add a plasticizer such as hydrophilic low molecular substance to the adhesive layer (2b) to impart suitable tackiness. Examples of the hydrophilic low molecular substance include liquid compounds having a high boiling point and deliquescent inorganic salts such as those mentioned above, which are used in the amounts mentioned above.

The above-mentioned adhesive layer (2b) may be crosslinked in the entirety as long as it satisfies the above-mentioned range of contact angle with water, and 5–75% by weight of the components constituting the adhesive layer may be a gel-like insoluble substance which cannot be dissolved in or eluted with water. This is because the adhesive layer of pressure sensitive adhesive sheet (1b) may fail to cohere when pressed against the test surface and peeled off, depending on the kind of water-soluble polymer to be used, and precise transfer and collection of microorganisms cannot be achieved.

In this case, the adhesive layer (2b) may be crosslinked by the addition of a crosslinking agent. Examples of the crosslinking agent include polyhydric epoxy compounds such as ethylene glycol diglycidyl ether, glycerine triglycidyl ether and triglycidyl isocyanurate, polyhydric isocyanate compounds such as CORONATE L and CORONATE HL (manufactured by NIPPON POLYURETHANE INDUSTRY CO., LTD.), benzoyl peroxide and the like. These crosslinking agents are added in an amount of 0.01–5 parts by weight per 100 parts by weight of the adhesive constituting the adhesive layer (2b).

Other methods for crosslinking the adhesive layer (2b) include, for example, insolubilization using electron beam or by irradiation (γ-ray) crosslinking. The adhesive face of the adhesive layer may be sterilized by, for example, exposure to radiation to decrease the background. The exposure to radiation results in sterilization and crosslinking. The exposure dose in this case is, for example, not less than 1 kGy, particularly not less than 25 kGy and not more than 50 kGy, in the case of acrylic copolymer. When it is less than 25 kGy, complete eradication of bacteria cannot be guaranteed, but when it is not less than 25 kGy, sterilization required by medical regulations can be simultaneously achieved. When it exceeds 50 kGy, the adhesive layer (2b) is unbeneficially deteriorated.

The adhesive layer (2b) has a peel adhesion of not less than 30 g/12 mm, preferably not less than 80 g/12 mm width, and not more than 600 g/12 mm width, preferably not more than 400 g/12 mm width, relative to a Bakelite board. When the adhesive strength is less than 30 g/12 mm width, microorganisms cannot be collected enough even by pressing the adhesive face against a test surface for desired transfer and capture of the microorganisms. When it exceeds 600 g/12 mm width, the adhesive layer (2b) may fail to cohere when pressed against the test surface and peeled off, and precise transfer and collection of microorganisms cannot be achieved.

The thickness of the adhesive layer (2b) is 10–100 $\mu$m, preferably 20–80 $\mu$m, more preferably 30–60 $\mu$m. When it is less than 10 $\mu$m, the desired adhesion on peeling cannot be attained, whereas when it exceeds 100 $\mu$m, the adhesive layer (2b) tends to show cohesive failure upon peeling.

The adhesive layer (2b) can contain a chromogenic substrate and/or chromogenic substance to be mentioned later.

The support (3b) is a sheet having a sufficient strength to endure bending. The support is subject to no particular limitation with regard to the material thereof, as long as it has flexibility allowing free application thereof by pressing the support as a pressure sensitive adhesive sheet (1b) against curved surfaces and narrow surfaces. For example, it may be a plastic film made from polyethylene, polypropylene, poryester, polyamide, polycarbonate, polysulfone, poly(vinyl chloride), polyurethane, ethylene vinylacetate copolymer, polytetrafluoroethylene, cellulose acetate, nitrocellulose and the like, or a woven fabric or nonwoven fabric prepared from a fiber made from the material polymer thereof. In addition, it may be a woven fabric, nonwoven fabric or paper prepared from natural materials, such as cotton fiber, hemp fiber and wool.

In this embodiment, the pressure sensitive adhesive sheet (1b) of the present invention can be produced by a method known per se. For example, an aqueous solution containing a water-soluble polymer and a hydrophilic or water-soluble low molecular substance is applied on a support and dried at 10° C.–200° C. to laminate an adhesive layer (2b) on the support (3b).

When the water-soluble polymer is an acrylic copolymer, it can be processed into a film or sheet by the above-mentioned extrusion molding (inflation molding, T die molding, lamination molding etc.).

Such sheet may be formed by calender method, casting method or other method. The film and sheet thus obtained can be cut into a desired shape and used as a pressure sensitive adhesive sheet (1b).

In the present invention, a water-soluble polymer is formed into a film or sheet and can be crosslinked by the irradiation of electron beam or $\gamma$-rays. Particularly when the water-soluble polymer is an acrylic copolymer, such irradiation crosslinking is effective, which can be applied under the same conditions as mentioned above.

The pressure sensitive adhesive sheet (1b) of the present invention can remain sterile when concealed, after sterilization, in a packaging material capable of shutting out microorganisms. The sterilization is preferably applied by EOG (ethylene oxide gas) method, electron beam method or $\gamma$-ray method. In this case, the exposure dose to radiation, such as electron beam and $\gamma$-ray, is adjusted according to the hydrophilicity of the polymer, wherein crosslinking can be applied under the same conditions as mentioned above.

For the method for detecting microorganisms of the present invention, any pressure sensitive adhesive sheet having an adhesive layer can be used, though preference is given to the pressure sensitive adhesive sheet of the present invention. The use of the pressure sensitive adhesive sheet of the present invention is explained in the following.

The microorganisms to be detected here include, for example, procaryotic microorganisms such as bacteria and actinomyces, eumycetes such as yeast and mold, lower algae, virus, and culture cells of plants and animals.

The detection of microorganisms using the pressure sensitive adhesive sheet of the present invention comprises bringing the adhesive face of said sheet into contact with the test surface by pressing same to transfer and collect the microorganisms thereon, such as bacteria, onto the adhesive face, bringing the microorganisms into contact with an aqueous solution containing a chromogenic reagent by application of a solution on the adhesive face, and detection and quantitative determination of the colored product.

The chromogenic reagent to be used in the present invention may vary depending on the mode of color development. For example, (1) an enzyme-labeled antibody and/or the corresponding chromogenic substrate, (2) an enzyme and/or the corresponding chromogenic substrate, or (3) a chromogenic substance which develops color by reaction with cell component contained in the test target microorganism can be used. According to the method of the present invention, microorganisms are stained on the surface of the adhesive layer, and observation of color produced and the amount of color production with naked eyes or by the use of a microscope or optical equipments reveals the presence or otherwise of microorganisms such as bacteria, as well as the number thereof, thus enabling real-time detection of microorganisms without the need of culture for colony formation and the like. The detection of microorganisms of one test surface according to the method of the present invention can be performed in 30 minutes.

For example, the pressure sensitive adhesive sheet (1a, 1b) of the present invention which is set on a roller is pressed against a test object, such as floor and wall, to transfer and collect the microorganisms attached to the test surface onto the roller. When a test surface considered to be involving less number of microorganisms is tested, the same adhesive face of the pressure sensitive adhesive sheet (1a, 1b) may be pressed plural times. One of the major effects of the method of the present invention is that accumulation of microorganisms is possible without culture, which is needed in the agar stamp method, or concern about the variation of microorganism flora due to the culture. Thus, a number of microorganisms can be collected simply by increasing the number of pressing, as, in the membrane filter method, the microorganisms dispersed in water are concentrated.

The pressure sensitive adhesive sheet (1a, 1b) with microorganisms attached thereto is cut into a predetermined size and the adhesive layer is brought into contact with a chromogenic reagent to allow microorganisms to produce color on the adhesive face. When the main component of the adhesive layer is a water-soluble polymer and the pressure sensitive adhesive sheet having said adhesive layer (1a) is dissolved in water, the pressure sensitive adhesive sheet with the microorganisms attached thereto is cut into a predetermined size and placed in a funnel of a filtration filter. Then, an aqueous solution containing a chromogenic reagent is filled therein, retained for a few minutes and filtered by suction. The redundant chromogenic reagent is washed away with water such as sterile water to leave only colored microorganisms on the water-permeable membrane (4). When a chromogenic substrate or chromogenic substance is added in advance to the adhesive layer (2a), washing with water such as sterile water for filtration is sufficient. The colored microorganisms are observed with a microscope, or observed after excitation when color produced is fluorescent or chromogenic substance is a fluorescent dye, whereby the number of microorganisms can be directly counted.

The detection or determination of microorganisms can be performed by visual observation using naked eyes. Alternatively, an optical image is formed by light microscope, fluorescence microscope, laser microscope or other suitable optical equipment, and the image is analyzed by a statistical method. Examples of other optical equipment include laser scanning sitometer which scans microorganisms at high speed with a laser beam and graphically shows the signal obtained from individual microorganisms. The method of the present invention is free of culture, so that the microorganisms on the adhesive face of the pressure sensitive adhesive sheet (1a, 1b) can be substantially detected in several to several dozen minutes.

Some of the methods for biochemical detection and quantitative determination of a trace component with high sensitivity using an enzyme and a substrate are well known. Among them are enzyme immunoassay wherein an enzyme-labeled antibody against a trace component in a microorganism is used and a method wherein the activity of an enzyme activated by the action of the trace component in a microorganism is used as an index (e.g., Limulus test which determines endotoxin of bacteria).

These methods are characterized by highly sensitive and specific detection achieved by the combination of a specific biochemical reaction of the detection target component in trace amounts and an enzymatic reaction. The present invention is based on these methods, wherein the cell component of the microorganisms transferred and collected on the adhesive face is biochemically and specifically reacted to produce color on the adhesive face, whereby highly sensitive identification and counting of microorganisms is performed with high precision.

When color is developed by the combination of an enzyme and a chromogenic substrate, an enzyme precursor (proenzyme), such as phenoloxidase and coagulase, which is activated by the action of a trace component in a microorganism, can be used as the enzyme. Preferred is prophenoloxidase derived from body fluids of silkworm and *Limulus polyphemus*. Since said body fluid has a cascade system wherein prophenoloxidase is activated on recognition of peptidoglycan and/or β-1,3-glucan, which are cell wall components of microorganisms, and phenoloxidase is produced, the phenoloxidase activity is determined using a chromogenic substrate for the detection and counting of microorganisms. When prophenoloxidase is used, the chromogenic substrate may be, for example, 3-(3,4-dihydroxyphenyl)alanine (hereinafter to be abbreviated as DOPA).

One method to determine phenoloxidase activity includes the use of the body fluid of silkworm. The body fluid of silkworm (silkworm larvae plasma) has a biological defence system called a phenoloxidase precursor cascade wherein peptidoglycan and (1→3)-β-glucan initiate a response that finally activates phenoloxidase (Masaaki Ashida, Biological Defense of Invertebrata, Japan Scientific Society Press, p. 111 (1992)). Examples of the reagent include SLP reagent manufactured by Waco Pure Chemical Industries, Ltd., which is a lyophilized product of aseptically harvested silkworm larvae plasma. The microorganisms can be detected and counted by melanin color development method using said reagent.

The SLP reagent contains hemolymph derived from silkworm larvae plasma (inclusive of complete prophenoloxidase activating cascade system mentioned above), and prophenoloxidase reacts with peptidoglycan and β-1,3-glucan in trace amounts with high sensitivity and is activated to phenoloxidase. The activated phenoloxidase forms melanin by oxidizing, with high sensitivity, a trace amount of DOPA added as a chromogenic substrate and develops black purple color. Using this SLP reagent, microorganisms are stained by applying or spraying an aqueous solution containing SLP reagent and DOPA to the adhesive face on which microorganisms have been collected. As a result, phenoloxidase in the SLP aqueous solution is activated according to the amounts of microorganisms trapped on the adhesive face and becomes black purple. The amounts (concentrations) of SLP reagent and chromogenic substrate DOPA are properly determined according to the amounts of microorganisms captured on the adhesive face. Naturally, greater amounts of microorganisms (higher concentrations) result in shorter time necessary for producing black purple color, and smaller amounts thereof result in longer time. It is also natural that greater amounts of microorganisms captured on the adhesive face lead to greater amounts of activated phenoloxidase, and thus nearly precise quantitative determination of the amounts of microorganisms on the adhesive face can be carried out by measuring the time necessary for producing black purple color. Though subject to variation depending on the kind of microorganisms, in the case of normal bacteria on the skin, *Staphylococcus epidermidis*, said time is 5–20 minutes when bacteria content is greater (not less than $10^4$ cells) and 60 minutes or longer when bacteria content is smaller (not more than $10^3$ cells). Visual observation here enables determination at the level of the order of the bacterial amount. When the adhesive face is scanned with high sensitivity at a high speed using an optical equipment to determine the amount of melanin produced and the result is compared with the calibration curve previously drawn, bacterial amounts can be quantitatively determined. In this case, filtration by suction of the chromogenic reagent, washing thereof and the like are preferably not done.

When an enzyme-labeled antibody and a chromogenic substrate are used for color development, the enzyme-labeled antibody contains an antibody against a component specifically contained in the detection target microorganism, which is preferably surface antigen of microorganisms, more preferably surface antigen of bacteria which has been covalently bound with an enzyme marker. By surface antigen of microorganism is meant an antigenic substance present on the cell surface of microorganism, such as peptidoglycan which is a bacterial cell wall component, lipopolysaccharide(endotoxin) which is an outer membrane component, and β-1,3-glucan which is an eumycete cell wall component. As the enzyme marker, alkaline phosphatase and peroxidase used for general enzyme immunoassay are exemplified. The chromogenic substrate may be 3,3',5,5'-tetramethylbenzidine (hereinafter to be referred to as TMB) or o-phenylenediamine when peroxidase is used as an enzyme, though selected according to the enzyme marker to be used. When alkaline phosphatase is used as an enzyme, a reagent containing 5-bromo-4-chloro-3-indolyl phosphate (BCIP) and nitro blue tetrazolium (hereinafter to be abbreviated as NBT) is exemplified. In this case, a reaction product of alkaline phosphatase and BCIP to be the substrate thereof reacts with NBT which is a chromogenic substrate to develop color. In addition, p-nitrophenyl phosphate is exemplified. By combining an enzyme-labeled antibody and a chromogenic substrate, one or more of the specific microorganisms can be detected and counted.

In the present invention, the enzyme-labeled antibody, enzyme and chromogenic substrate need not be contained in a single aqueous solution, but may be contained in a combination of an aqueous solution containing enzyme-labeled antibody or enzyme and an aqueous solution containing chromogenic substrate. Particularly when enzyme-labeled antibody and chromogenic substrate are combined for use, a higher specificity can be attained by using such two respective kinds of aqueous solutions. When chromogenic substrate is contained in the adhesive layer, only an aqueous solution containing enzyme-labeled antibody or enzyme may be brought into contact with the adhesive face of the pressure sensitive adhesive sheets (1a, 1b).

According to the method of the present invention using a chromogenic substance as a chromogenic reagent, the substance specifically acts on the cell component of the detection target microorganisms to produce color. Typical examples thereof include fluorescent dye which stains nucleic acid and protein. Other chromogenic dyes include fluorescent nucleotide analog, fluorescent dye to stain nucleic acid, dye to stain protein, environmental fluorescent probe used for structural analysis of protein, dye used for analysis of cell membrane and membrane potential, dye used for labeling of fluorescent antibody, and the like when microorganisms in general are to be tested; dye which develops color by respiration of cells, and the like when aerobic bacteria are to be tested; dye which stains mitochondria, dye which stains Golgi's apparatus, dye which stains endoplasmic reticulum, dye which reacts with intracellular esterase and modified compounds thereof, and the like when eukaryotic microorganisms are to be tested, and dye used for observation of bone tissues, dye which is a nerve cell tracer, and the like when cells of higher animal are to be tested; all of which can be observed with a fluorescent microscope.

By properly determining the kind of these chromogenic substances, the method of the invention can be applied to a wide range of uses such as all cell count determination wherein all microorganisms are detected, detection to stain and count only microorganisms having respiratory activity, detection to stain and count only microorganisms having esterase activity, and detection to stain and count specific genera and species of microorganisms utilizing double staining method combining plural chromogenic substances.

For example, the pressure sensitive adhesive sheet of the present invention can be applied to a test face to transfer the microorganisms present on the test face, and the microorganisms can be stained without preculture, thereby allowing observation of microorganisms as single cells. Therefore, the present method can be used for environmental investigations wherein the cleanliness of the test object should be quickly determined. In addition, recovery of microorganisms at a single cell level enables accumulation and concentration of microorganisms by pressing the pressure sensitive adhesive sheet plural times against the test face, and makes the sheet of the present invention practical. The sheet of the present invention can be applied to environmental microorganism detection in the medical field, food industry field and the like.

The present invention is described in more detail by way of Examples, which should not be construed as limiting the invention.

EXAMPLE 1

Acrylic acid (60 parts by weight), 2-methoxyethyl acrylate (100 parts by weight), butyl acrylate (40 parts by weight), benzoyl peroxide (0.6 part by weight), toluene (240 parts by weight) and isopropyl alcohol (60 parts by weight) were charged in a 1 l flask equipped with an agitator, a thermometer, a reflux condenser and a nitrogen gas blowing nozzle, and polymerized under a nitrogen flow at 59° C.–62° C. for 12 hours. Isopropyl alcohol (37.5 parts by weight) and water (25 parts by weight) were added to the obtained reaction mixture (100 parts by weight), and an aqueous solution of sodium hydroxide (5.33 parts by weight) in water (20 parts by weight) was dropwise added. The obtained mixture was applied to a release paper and dried to give a 50 $\mu$m thick pressure sensitive adhesive sheet.

This pressure sensitive adhesive sheet was laminated on a cellulose acetate membrane having an average pore size of 0.45 $\mu$m. A release paper was peeled off from the obtained pressure sensitive adhesive sheet, and the pressure sensitive adhesive sheet was pressed five times against the same surface of a bed sheet to collect microorganisms.

The pressure sensitive adhesive sheet was set in a funnel with the adhesive layer facing up, and 3 ml of a 1 ppm 4,6-diamino-2-phenyl-indole aqueous solution (dye solution) was applied. After 3 minutes, the solution was filtered by suction.

Inasmuch as the adhesive pressure sensitive adhesive sheet was dissolved in the dye solution, only the stained microorganisms were trapped and accumulated on the cellulose acetate membrane. The microorganisms were observed and counted using a fluorescene microscope, and the number of stained microorganisms was found to be $3 \times 10^4$ cells/cm$^2$.

EXAMPLE 2

Polyoxypropylene glyceryl ether (50 parts by weight, Sannikkusu SP-750 manufactured by SANYO CHEMICAL INDUSTRIES, LTD.) and potassium persulfate (1 part by weight) were dissolved in water (300 parts by weight), and acrylic acid (100 parts by weight) was added. The mixture was placed in a 1 l flask equipped with an agitator, a thermometer, a reflux condenser and a nitrogen gas blowing nozzle. Then, the mixture was retained in a nitrogen flow at 60° C. and allowed to polymerize for 8 hours with agitation. An aqueous solution of potassium hydroxide (2.1 parts by weight) in water (20 parts by weight) and Sannikkusu SP-750 (55 parts by weight) were added to the resulting mixture (100 parts by weight).

The obtained mixture was applied to a 80 $\mu$m thick polyester film and dried to give a 30 $\mu$m thick pressure sensitive adhesive sheet.

This pressure sensitive adhesive sheet was laminated on a polycarbonate filter having an average pore size of 0.45 $\mu$m. The polyester film of the obtained pressure sensitive adhesive sheet was peeled off, and the pressure sensitive adhesive sheet was pressed ten times against different surfaces of a floor made from a synthetic resin to collect microorganisms.

The pressure sensitive adhesive sheet was set in a funnel with the adhesive layer facing up, and 3 ml of an aqueous solution of 1 ppm 5-cyano-2,3-ditolyl-tetrazolium chloride (dye solution) was applied. After 3 minutes, the solution was filtered by suction.

Inasmuch as the adhesive of the adhesive pressure sensitive adhesive sheet was dissolved in the dye solution, only the stained microorganisms were collected and accumulated on the polycarbonate filter. The microorganisms were observed and counted using a fluorescene microscope, and the number of stained microorganisms was found to be $5 \times 10^5$ cells/cm$^2$.

EXAMPLE 3

2-Methoxyethyl acrylate (70 parts by weight), N-vinyl-2-pyrrolidone (30 parts by weight), azoisobutyronitrile (0.175 parts by weight) as an initiator and a mixed solvent of distilled water:methanol:isopropanol (250 parts by weight, weight ratio 16:23:1) were charged in a closed type reactor equipped with an agitator, and the inside of the reactor was displaced with nitrogen, which was followed by polymerization for 5 hours while keeping the temperature therein at 60° C.–62° C. The mixture was cooled to room temperature to give a solution of acrylic copolymer.

Thereto was added polyoxypropylene glyceryl ether (20 parts by weight, average molecular weight 400). Then, a 4,6-diamino-2-phenyl-indole aqueous solution (dye solution) was added to a final concentration of 1 ppm.

This solution containing the acrylic copolymer was applied in a uniform thickness to a release paper, and dried at 130° C. for 5 minutes to give a 50 μm thick pressure sensitive adhesive sheet. A 10 μm thick polycarbonate filter having a pore size of 0.2 μm was laminated on the adhesive layer of this pressure sensitive sheet. Then, a reinforcing filter having a pore size of 20 μm and thickness of 200 μm was laminated on the polycarbonate filter to give a pressure sensitive adhesive sheet of the present invention.

A suspension (10 μl) of *Escherichia coli* (*E. coli*) ($1.6 \times 10^8$ cells/cm$^2$) was applied to a rigid poly(vinyl chloride) board and dried. The adhesive face of said pressure sensitive adhesive sheet was pressed different number of times against the board to collect microorganisms. The pressure sensitive adhesive sheet was set in a funnel with the adhesive layer facing up, and sterile water was applied. After 3 minutes, water was filtered by suction.

Inasmuch as the adhesive of the adhesive pressure sensitive adhesive sheet was dissolved in sterile water, only the stained microorganisms were collected and accumulated on the polycarbonate filter. The reinforcing filter was peeled off and the obtained filter was observed with a fluorescene microscope and stained microorganisms were counted. The results are shown in Table 1.

TABLE 1

| number of pressing | 1 | 2 | 5 | 10 |
|---|---|---|---|---|
| recovery (%) of *E. coli* | 27 | 67 | 62 | 74 |

EXAMPLE 4

To a polyoxypropylene glyceryl ether-added acrylic copolymer solution obtained in the same manner as in Example 3 were added 4,6-diamino-2-phenyl-indole aqueous solution and 6-carboxyfluorescein diacetate aqueous solution to final concentrations of 1 ppm and 150 ppm, respectively.

In the same manner as in Example 3 except that the solutions were dried at 40° C. for one hour, pressure sensitive adhesive sheets having a thickness of adhesive layer of 30 μm were obtained.

The release papers of these pressure sensitive sheets were peeled off, and the adhesive face was pressed three times against human hand to collect microorganisms. The pressure sensitive adhesive sheet was set in a funnel with the adhesive layer facing up, and sterile 0.1 M phosphate buffer (pH 8.5) containing 10 mM EDTA sodium salt was applied. After 3 minutes, said solution was filtered by suction.

Inasmuch as the adhesive of the adhesive pressure sensitive adhesive sheet was dissolved in sterile buffer, only the microorganisms stained with two kinds of dyes were collected and accumulated on the polycarbonate filter. The reinforcing filter was peeled off and the obtained polycarbonate filters were observed with a fluorescene microscope. The two dyes required different dyeing operations, wherein nucleic acid dyeing by 4,6-diamino-2-phenyl-indole aqueous solution resulted in fluorescently dyed bacterial cells inclusive of dead cells, whereas 6-carboxyfluorescein diacetate fluorescently dyed esterase activated cells alone. The different fluorescent color allowed easy division of the cells.

Using the same sample, each was subjected to observation, as a result of which the whole cell number of the microorganisms was $4 \times 10^5$ cells/cm$^2$ and esterase activated cells were $3 \times 10^4$ cells/cm$^2$.

EXAMPLE 5

2-Methoxyethyl acrylate (70 parts by weight), N-vinyl-2-pyrrolidone (30 parts by weight), azobisisobutyronitrile (0.175 part by weight) as an initiator and a mixed solvent of distilled water:methanol:isopropanol (250 parts by weight, weight ratio 16:23:1) were charged in a closed type reactor equipped with an agitator, and the inside of the reactor was displaced with nitrogen, which was followed by polymerization for 1.5 hours while keeping the temperature therein at 60° C.–62° C. Then, two hours of agitation at 75° C. completed the reaction. The mixture was cooled to room temperature to give a solution of acrylic copolymer.

Thereto was added polyoxypropylene glyceryl ether (20 parts by weight, average molecular weight 400). This solution containing acrylic copolymer was applied in a constant thickness to a 20 μm thick polyester nonwoven fabric which was flexible but strong against bending, and dried at 130° C. for 10 minutes to give a pressure sensitive adhesive sheet having a thickness of adhesive layer of 50 μm. The amount of 2-methoxyethyl acrylate and N-vinyl-2-pyrrolidone of the adhesive layer was not more than 10 ppm by weight and 200 ppm by weight, respectively. The adhesive strength against a Bakelite board was 80 g/12 mm width.

Distilled water was dropwise added to the adhesive face of the obtained pressure sensitive adhesive sheet, and initial contact angle was determined 30 seconds later at 25° C. to find the angle to be substantially 0°, thus confirming that the adhesive face had complete wettability by water. The contact angle was determined by a FACE automatic contact angle meter CA-X type manufactured by KYOWA INTERFACE SCIENCE CO., LTD.

This pressure sensitive adhesive sheet was cut out in two discs having a diameter of 25 mm. One of them was pressed three times against the same part of human face skin. Transparent ethylene polyterephthalate (PET) film rings (thickness 0.3 mm), which had been cut out in an outer diameter of 25 mm and inner diameter of 15 mm, were concentrically placed on the adhesive face of the circular pressure sensitive adhesive sheet to give samples having a liquid residence concentric pot at about the center of the circular pressure sensitive adhesive sheet.

To this liquid residence pot was dropwise added 20 μl of an aqueous solution containing SLP reagent and DOPA with a pipet to extend said solution over the entirety of the pot, which was followed by preservation and monitoring under an atmospheric environment at 30° C. The circular liquid residence pot became black purple in about 13 minutes.

The other disk was treated in the same manner as above except that it was not pressed against human face skin, to give a blank sample which was treated with SLP reagent in the same manner. As a result, the liquid residence pot became black purple in about 60 minutes.

According to a different publication, Journal of Antibacterial and Antifungal Agents, Japan, Vol. 22 (No. 3), 13–18 (1994), human face skin is known to have microorganisms inclusive of bacteria such as *Staphylococcus epidermidis* at the level of $10^4$–$10^5$ cells/cm$^2$.

EXAMPLE 6

In the same manner as in Example 5 except that polyoxypropylene glyceryl ether (30 parts by weight, average molecular weight 400) was added, a solution containing acrylic copolymer was obtained. This acrylic copolymer solution was applied on a 10 μm thick PET film in a uniform thickness, and dried at 130° C. for 10 minutes to give a PET film having a 40 μm thick adhesive layer on one side. This PET film was placed in a suitable bag capable of retaining sterile condition. Exposure to 35 kGy T-ray resulted in complete sterilization and crosslinking of the adhesive layer, whereby a pressure sensitive adhesive sheet was obtained. The adhesive strength to a Bakelite board was 110 g/12 mm width.

A 25 mm diameter disc was punched out from the obtained pressure sensitive adhesive sheet and immersed in a sufficient amount of distilled water for 2 hours. The crosslinking degree of the adhesive layer was determined as the percentage of gel insoluble in water (hereinafter also referred to as gel fraction). As a result, the gel fraction of the adhesive layer was 52%. The initial contact angle of the adhesive face of the pressure sensitive adhesive sheet with distilled water was substantially 0° by the determination in the same manner as in Example 5, and it was confirmed that the adhesive face had complete wettability by water.

Using this pressure sensitive adhesive sheet and in the same manner as in Example 5, the adhesive face was pressed three times against human face skin. A circular sample was prepared by placing a PET film ring thereon to form a concentric liquid residence pot, and a blank sample was prepared by placing a PET film ring on the adhesive face which was not pressed against human face skin, to form a concentric liquid residence pot.

These two samples were treated in the same manner as in Example 5 and brought into contact with an aqueous solution containing an SLP reagent and DOPA. The time necessary for black purple color development at a certain absorbance level was measured using an optical instrument. Comparison with the calibration curve drawn in advance based on the determination using the same optical instrument revealed the amount of microorganisms as converted to the amount of *Staphylococcus epidermidis* on the human skin. As a result, the blank sample showed the presence of $8 \times 10^2$ cells/cm$^2$ of microorganisms and the sample pressed against human face skin showed the presence of $9 \times 10^4$ cells/cm$^2$ of microorganisms.

EXAMPLE 7

A commercially available aqueous poly(acrylic acid) copolymer solution (100.5 g, solid concentration 20%, trademark Julymer AC-10H manufactured by NIHON JUNYAKU CO., LTD.) was dissolved in water (84 g). To this solution were added and dissolved poly(acrylic acid) powder (86 g, trademark Julymer AC-10LP manufactured by NIHON JUNYAKU CO., LTD.) having different average molecular weight and glycerin (217 g) while heating. Then, NaOH (35 g) was added to give a mixed aqueous solution of sodium polyacrylate/glycerin having an about 60 saponification degree.

Triglycidyl isocyanulate (0.34 part by weight) was dissolved in water and added to this mixed solution (100 parts by weight) as a reactive crosslinking agent to give a viscous aqueous solution having a concentration of sodium polyacrylate of 20 wt %.

A polyester nonwoven fabric having a thickness of 30 μm was laminated on one side of a 30 μm thick polypropylene film to give a laminate film. The above-mentioned viscous aqueous solution was applied on the polyester nonwoven fabric side of this laminate film in a uniform thickness using a fountain coater. The film was dried in a drier at 100° C. for 10 minutes and successively wound up. Then, the film was heated at 50° C. for 10 hours for maturation to give a pressure sensitive adhesive sheet. The thickness of the adhesive layer was 50 μm and the adhesive strength to a Bakelite board was 200 g/12 mm width.

A 25 mm diameter disc was punched out from the obtained pressure sensitive adhesive sheet and the crosslinking degree of the adhesive layer was determined in the same manner as in Example 6 as the percentage of gel insoluble in water. As a result, the gel fraction of the adhesive layer was 48%. The initial contact angle of the adhesive face of the pressure sensitive adhesive sheet with distilled water was determined in the same manner as in Example 5 and found to be substantially 0°. Thus, it was confirmed that the adhesive face had complete wettability by water.

Separately, a test object was prepared by forming a bacterial colony at a surface concentration of *Escherichia coli* $1 \times 10^8$ cells/cm$^2$ on a PET film, and a blank test object was prepared without forming an *Escherichia coli* colony on a PET film. In the same manner as in Example 5, the pressure sensitive adhesive sheet obtained in this Example was pressed twice against the same site of the film where the above-mentioned *Escherichia coli* colony had been formed, and a PET film ring was placed thereon to give a circular sample having a liquid residence pot. In the same manner as above, the sheet was pressed twice against the same site of the blank test object and a blank sample was prepared.

A predetermined amount of an aqueous solution containing SLP reagent and DOPA was sprayed on the liquid residence pots of these two samples, and the samples were preserved and monitored under an atmospheric environment at 30° C.

The test object with an *Escherichia coli* colony became black purple in about 15 minutes, and the blank test object became black purple in about 2 hours.

As is evident from these results, visual observation of the color development and measuring the time up to the color development enabled evaluation of the presence or otherwise of bacterial colony. As the results show, the blank test object also became black purple with the passage of time, which means that even in the absence of a bacterial colony under normal environment, microorganisms such as bacteria were present.

EXAMPLE 8

Butyl acrylate (95 parts by weight), acrylic acid (5 parts by weight), azobisisobutyronitrile (0.175 part by weight) as an initiator and ethyl acetate solvent (250 parts by weight) were charged in a closed type reactor equipped with an agitator, and the inside of the reactor was displaced with nitrogen, which was followed by polymerization for 1.5 hours while keeping the temperature therein at 60° C.–62° C. Then, two hours of agitation at 75° C. completed the reaction. The mixture was cooled to room temperature to give a viscous solution of acrylic copolymer.

To 100 parts by weight of the viscous solution was added benzoyl peroxide (0.2 part by weight) which was thoroughly dissolved by stirring at 25° C. for 15 minutes. A polyester nonwoven fabric having a thickness of 30 μm was laminated on one side of a 10 μm thick polyplopylene film to give a laminate film. The above-mentioned viscous aqueous solution was applied on the polyester nonwoven fabric side of this laminate film in a uniform thickness using a fountain coater. The film was dried in a drier at 110° C. for 10 minutes to give a pressure sensitive adhesive sheet. The thickness of the adhesive layer was 50 µm and the adhesive strength to a Bakelite board was 450 g/12 mm width.

A 25 mm diameter disc was punched out from the obtained pressure sensitive adhesive sheet and immersed in a sufficient amount of toluene for 2 hours. The crosslinking degree of the adhesive layer was determined as the percentage of gel insoluble in toluene. As a result, the gel fraction of the adhesive layer was 58%. The initial contact angle of the adhesive face of the pressure sensitive adhesive sheet with distilled water was 83°, and it was confirmed that the adhesive face had medium level of wettability by water.

A test object was prepared by forming a bacterial colony at a surface concentration of *Escherichia coli* 1×10$^6$ cells/cm$^2$ on a PET film, and a sterile PET film was prepared as a blank test object.

In the same manner as in Example 5, the pressure sensitive adhesive sheet obtained in this Example was pressed once against the same site of the film where the above-mentioned Escherichia coli colony had been formed, and a PET film ring was placed thereon to give a circular sample having a liquid residence pot. In the same manner as above, the sheet was pressed once against the same site of the blank test object and a blank sample was prepared. To these liquid residence concentric pots was dropwise added 50 µl of an aqueous solution containing SLP reagent and DOPA, which was followed by preservation and monitoring under an atmospheric environment at 25° C.

The sample with an *Escherichia coli* colony became black purple in about 20 minutes, but the blank sample did not become black purple even after 3 hours.

As is evident from these results, visual observation of the color development and measuring time up to the color development led to the evaluation of the presence or otherwise of bacterial colony.

EXAMPLE 9

DOPA (2 parts by weight) was added to a solution (100 parts by weight) containing the acrylic copolymer obtained in Example 5. The mixture was applied on a polyethylene foam (thickness 10 mm) in a uniform thickness and dried at 50° C. for 30 minutes to give an adhesive foam having a thickness of the adhesive of 50 µm. The adhesive strength of this foam to a Bakelite board was 76 g/12 mm width and the initial contact angle of the adhesive sheet with distilled water as determined in the same manner as in Example 5 was substantially 0°.

This adhesive foam was cut out in two discs having a diameter of 25 mm. One of them was pressed three times against the same part of human face. An SLP reagent (100 µl) without DOPA was dropwise added on the adhesive face and color production was checked under an atmospheric environment at 30° C.

The sample pressed against face became black purple in about 16 minutes, but the blank sample did not become black purple even after 3 hours.

EXAMPLE 10

A peroxidase-labeled anti-*Escherichia coli* antibody solution (100 µl, manufactured by ViroStat) was dropwise added on the adhesive face of the two samples obtained in Example 7, and the samples were left standing at room temperature for 5 minutes. Then, the adhesive face was thoroughly washed with a 0.05 mol/l phosphate buffer to remove unreacted antibody. Then, using a TMB substrate kit (manufactured by Vector Laboratories), color production was observed.

The sample with *Escherichia coli* showed color production by visual observation in 60 seconds after addition of the substrate, but the blank sample did not show color even after 5 minutes.

EXAMPLE 11

In the same manner as in Example 7 except that the bacteria on the PET film was *Escherichia coli* 0157:H7, alkaline phosphotase-labeled anti-*Escherichia coli* 0157:H7 antibody (manufactured by Kirkegaard and Perry Laboratories) buffer (antibody 1 mg/ml) was dropwise added by 100 µl to the adhesive face of the two kinds of samples, and the samples were stood still for 5 minutes at room temperature. Then, the adhesive face was thoroughly washed with 0.05 mol/l phosphate buffer to remove unreacted antibody. Then, using a BICP/NBT phosphatase substrate system (manufactured by Kirkegaard and Perry Laboratories), color production was observed.

The sample with *Escherichia coli* 0157:H7 showed color production by visual observation in 60 seconds after addition of the substrate, but the blank sample did not show color even after 5 minutes.

EXAMPLE 12

In the same manner as in Example 5 except that polyoxypropylene glyceryl ether (30 parts by weight, average molecular weight 400) was added, a solution containing acrylic copolymer was obtained. This acrylic copolymer solution was applied on a PET film (thickness 10 µm) in a uniform thickness and dried at 130° C. for 5 minutes to give a PET film having a 60 µm thick adhesive layer on one side. This PET film was placed in a suitable bag capable of retaining sterile condition. Exposure to 35 kGy T-ray resulted in complete sterilization and crosslinking of adhesive layer, whereby a pressure sensitive adhesive sheet was obtained. The adhesive strength to a Bakelite board was 140 g/12 mm width.

A 25 mm diameter disc was punched out from the obtained pressure sensitive adhesive sheet and immersed in a sufficient amount of distilled water for 2 hours. The crosslinking degree of the adhesive layer was determined as the percentage of gel insoluble in water. As a result, the gel fraction of the adhesive layer was 52%. The initial contact angle of the adhesive face of the pressure sensitive adhesive sheet with distilled water as determined in the same manner as in Example 5 was substantially 0°. Thus, it was confirmed that the adhesive face had complete wettability by water.

Using this pressure sensitive adhesive sheet and in the same manner as in Example 5, the adhesive face was pressed three times against human face skin. A circle sample was prepared by placing a PET film ring thereon and forming a concentric liquid residence pot, and a blank sample was prepared by placing a PET film ring on the adhesive face which was not pressed against human face skin and forming a concentric liquid residence pot.

These two samples were treated in the same manner and brought into contact with an aqueous solution containing an SLP reagent and DOPA, and the time necessary for black purple color development at a certain absorbance was measured using an optical instrument. Comparison with the calibration curve drawn in advance based on the determination using the same optical instrument revealed the amount of microorganisms as converted to the amount of *Staphylococcus epidermidis* on human skin. As a result, the blank sample showed the presence of 8×10 cells/cm$^2$ of microorganisms and the sample pressed against human face skin showed the presence of 9×10$^5$ cells/cm$^2$ of microorganisms.

The method for detecting microorganisms of the present invention enables real-time monitoring without culture of microorganisms, and is not limited to the detection of viable cells alone. Inasmuch as a contact of the pressure sensitive adhesive sheet with a test face results in accumulation of microorganisms, the manipulation is simple. In addition, by properly determining a chromogenic reagent, a specific microorganism alone can be detected and counted, so that it can be applied to environmental investigation in the medical field and food industry field.

When the pressure sensitive adhesive sheet of the present invention combining a water soluble adhesive layer mainly composed of a water-soluble polymer and a water-permeable membrane is used, it is possible to colonize only stained microorganisms alone on the water-permeable membrane and to directly count the stained microorganisms alone using, for example, a fluorescene microscope. In addition, the pressure sensitive adhesive sheet of the present invention wherein the contact angle of the adhesive layer surface with water is not more than 90° permits easy expansion of an aqueous solution containing a chromogenic reagent on the adhesive face, and the method of the present invention is practically advantageous.

This application is based on application Nos. 169279/1996, 169281/1996, 129580/1997 and 129586/1997 filed in Japan, the contents of which are incorporated hereinto by reference.

What is claimed is:

1. A pressure sensitive adhesive sheet for the detection of microorganisms, comprising a laminate of an adhesive layer mainly composed of a water-soluble polymer and a water-permeable membrane which does not allow passage of the microorganisms, wherein said water-soluble polymer is an acrylic copolymer containing alkoxyalkyl acrylate as a monomer component and the alkoxyalkyl acrylate is contained in a proportion of 60–80 wt % of the entire acrylic copolymer and said sheet has a thickness of 10–100 μm and an adhesive strength to a Bakelite board of 30 g/12 mm width to 600 g/12 mm width.

2. The sheet of claim 1, wherein the water-permeable membrane is supported by a water-permeable support.

3. The sheet of claim 2, wherein the surface of the adhesive layer has a contact angle with water of not more than 90°.

4. The sheet of claim 1, wherein the water-soluble polymer is easily dissolved in water and passes through the water-permeable membrane when dissolved in water.

5. The sheet of claim 1, wherein the surface of the water-permeable membrane on the adhesive layer side has a smoothness of not more than 20 μm.

6. The sheet of claim 1, wherein the surface of the adhesive layer has a contact angle with water of not more than 90°.

7. The sheet of claim 1, wherein the adhesive layer comprises a chromogenic substrate.

8. The sheet of claim 7, wherein the chromogenic substrate is one member selected from the group consisting of 3-(3,4-dihydroxyphenyl)-alanine, 3,3',5,5'-tetramethylbenzidine and nitro blue tetrazolium.

9. The sheet of claim 1, wherein the adhesive layer comprises an enzyme.

10. The sheet of claim 9, wherein the enzyme is a phenoloxidase.

11. The sheet of claim 1, wherein the adhesive layer comprises a chromogenic substrate and an enzyme.

12. The sheet of claim 1, wherein the adhesive layer comprises an enzyme-labeled antibody.

13. The sheet of claim 12, wherein the enzyme-labeled antibody is against a microorganism surface antigen and labeled with a peroxidase or alkaline phosphatase.

14. The sheet of claim 1, wherein the adhesive layer comprises an enzyme-labeled antibody and a chromogenic substrate.

15. The sheet of claim 1, wherein the adhesive layer comprises a chromogenic substance.

16. The sheet of claim 15, wherein the chromogenic substance is a fluorescent dye.

17. A pressure sensitive adhesive sheet for the detection of microorganisms, comprising an adhesive layer having a contact angle with water of not more than 90° and a support, the adhesive layer being formed on the support, wherein said water-soluble polymer is an acrylic copolymer containing alkoxyalkyl acrylate as a monomer component and the alkoxyalkyl acrylate is contained in a proportion of 60–80 wt % of the entire acrylic copolymer and said sheet has a thickness of 10–100 μm and an adhesive strength to a Bakelite board of 30 g/12 mm width to 600 g/12 mm width.

18. The sheet of claim 17, wherein the adhesive layer comprises a chromogenic substrate.

19. The sheet of claim 18, wherein the chromogenic substrate is one member selected from the group consisting of 3-(3,4-dihydroxyphenyl)-alanine, 3,3',5,5'-tetramethylbenzidine and nitro blue tetrazolium.

20. The sheet of claim 17, wherein the adhesive layer comprises an enzyme.

21. The sheet of claim 20, wherein the enzyme is a phenoloxidase.

22. The sheet of claim 17, wherein the adhesive layer comprises a chromogenic substrate and an enzyme.

23. The sheet of claim 17, wherein the adhesive layer comprises an enzyme-labeled antibody.

24. The sheet of claim 23, wherein the enzyme-labeled antibody is against a microorganism surface antigen and labeled with a peroxidase or alkaline phosphatase.

25. The sheet of claim 17, wherein the adhesive layer comprises an enzyme-labeled antibody and a chromogenic substrate.

26. The sheet of claim 17, wherein the adhesive layer comprises a chromogenic substance.

27. The sheet of claim 26, wherein the chromogenic substance is a fluorescent dye.

* * * * *